(12) United States Patent
Yeum et al.

(10) Patent No.: US 10,472,481 B2
(45) Date of Patent: Nov. 12, 2019

(54) METHOD FOR PREPARING FUNCTIONAL EXTRACT-CONTAINING POLYVINYL ALCOHOL FILM BY HETEROGENEOUS SAPONIFICATION OF POLYVINYL ACETATE FILM

(71) Applicant: Kyungpook National University Industry-Academic Cooperation Foundation, Daegu (KR)

(72) Inventors: Jeong Hyun Yeum, Daegu (KR); Seong Beak Yang, Gyeongsangbuk-do (KR); Sung Hun Yoo, Gyeongsangnam-do (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 67 days.

(21) Appl. No.: 15/553,347

(22) PCT Filed: Feb. 26, 2016

(86) PCT No.: PCT/KR2016/001963
§ 371 (c)(1),
(2) Date: Aug. 24, 2017

(87) PCT Pub. No.: WO2016/137292
PCT Pub. Date: Sep. 1, 2016

(65) Prior Publication Data
US 2018/0072859 A1    Mar. 15, 2018

(30) Foreign Application Priority Data

Feb. 27, 2015  (KR) .................. 10-2015-0028140

(51) Int. Cl.
| | | |
|---|---|---|
| *A01N 25/10* | (2006.01) | |
| *A01N 65/00* | (2009.01) | |
| *A61K 36/07* | (2006.01) | |
| *A61K 36/899* | (2006.01) | |
| *A61K 9/70* | (2006.01) | |
| *C08J 7/14* | (2006.01) | |
| *C08J 5/18* | (2006.01) | |
| *C08L 29/04* | (2006.01) | |
| *A01N 65/44* | (2009.01) | |
| *A61K 36/00* | (2006.01) | |

(52) U.S. Cl.
CPC ............. *C08J 7/14* (2013.01); *A01N 25/10* (2013.01); *A01N 65/00* (2013.01); *A01N 65/44* (2013.01); *A61K 9/7007* (2013.01); *A61K 36/07* (2013.01); *A61K 36/899* (2013.01); *C08J 5/18* (2013.01); *C08L 29/04* (2013.01); *A61K 36/00* (2013.01); *A61K 2236/33* (2013.01); *C08J 2329/04* (2013.01)

(58) Field of Classification Search
CPC .... C08J 7/14; C08J 5/18; A01N 25/10; A01N 65/00; A01N 65/44; A61K 36/899; A61K 9/7007; C08L 29/04
See application file for complete search history.

(56) References Cited

U.S. PATENT DOCUMENTS

| 2,936,488 A | * | 5/1960 | Cottet |
| 5,691,015 A | | 11/1997 | Tsukamoto et al. |

FOREIGN PATENT DOCUMENTS

| JP | 1993-093092 | 4/1993 |
| JP | 2005-194295 | 7/2005 |
| KR | 10-2002-0069054 | 7/2004 |
| KR | 10-0440601 | 7/2004 |
| KR | 10-2011-0105803 | 4/2013 |
| KR | 10-2007-0048405 | 6/2014 |
| KR | 10-2014-0077528 | 12/2015 |

OTHER PUBLICATIONS

Beringhs et al. (AAPS PharmSciTech, vol. 14, No. 1, Mar. 2013, pp. 445-455) (Year: 2013).*
International Search Report in related PCT Application Serial No. PCT/KR2016/001963, dated Jul. 1, 2016 (English translation attached).

* cited by examiner

*Primary Examiner* — Alma Pipic
(74) *Attorney, Agent, or Firm* — Hovey Williams LLP

(57) ABSTRACT

The present invention relates to a method for preparing a functional extract-containing polyvinyl alcohol film, which has an improved specific surface area by having a wrinkled form, and specifically, to a method for preparing a functional extract-containing polyvinyl alcohol film having wrinkles formed on a surface thereof, which comprises saponifying a functional extract-containing polyvinyl acetate film, while the functional extract-containing polyvinyl acetate film is immersed in a first solvent capable of maintaining the film form of the functional extract-containing polyvinyl acetate film, so as to convert the functional extract-containing polyvinyl acetate film into a functional extract-containing polyvinyl alcohol film.

14 Claims, 3 Drawing Sheets

[FIG. 1]
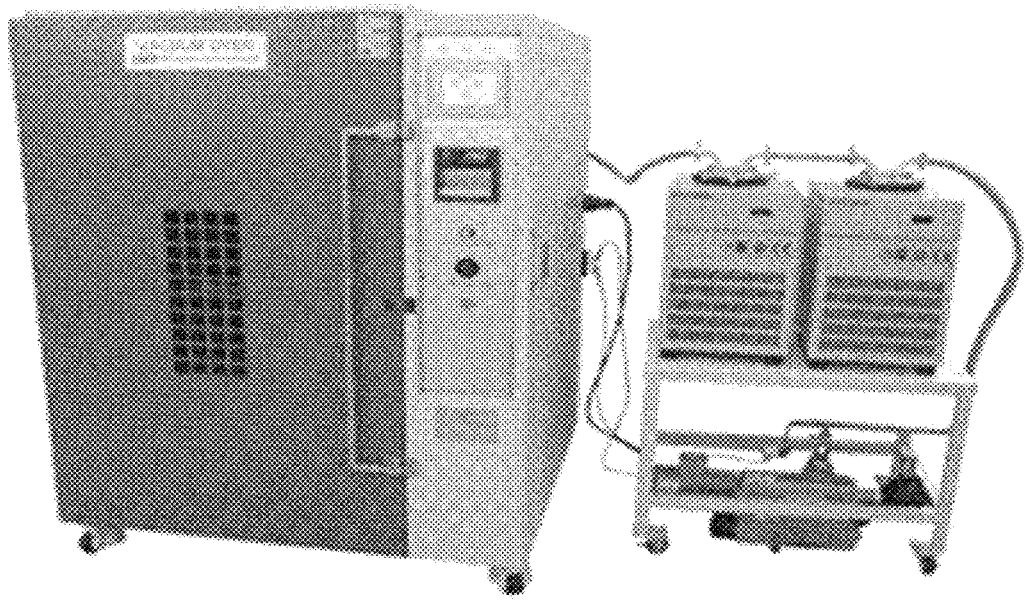
[FIG. 2]
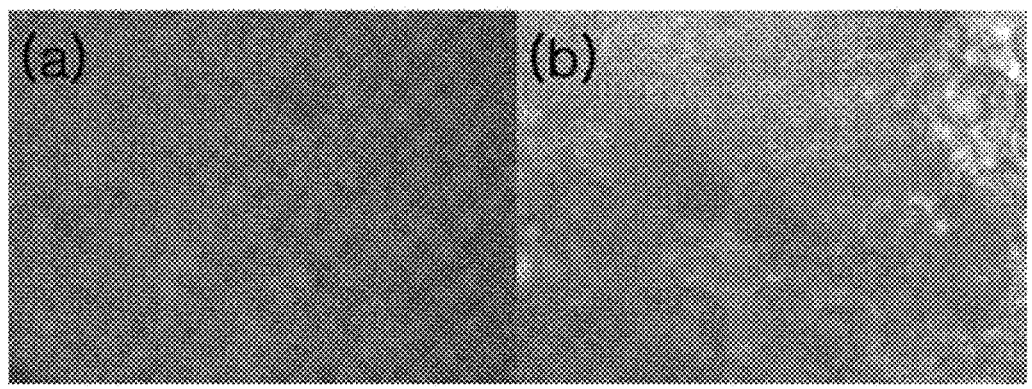

[FIG. 3]
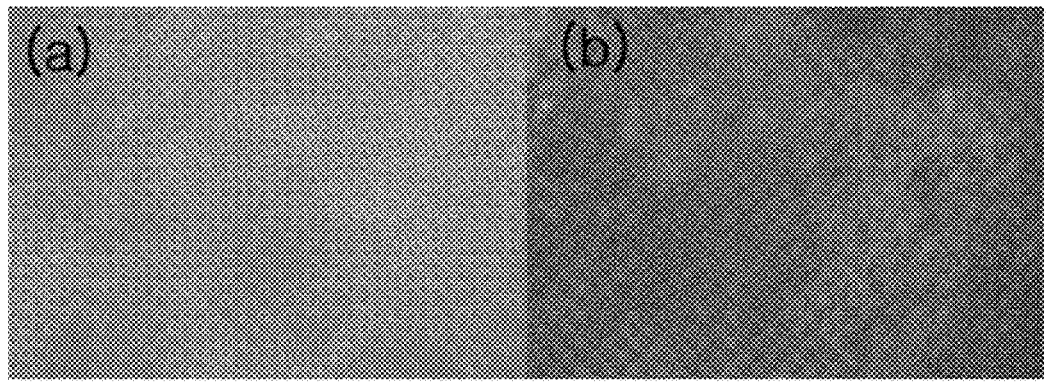
[FIG. 4]
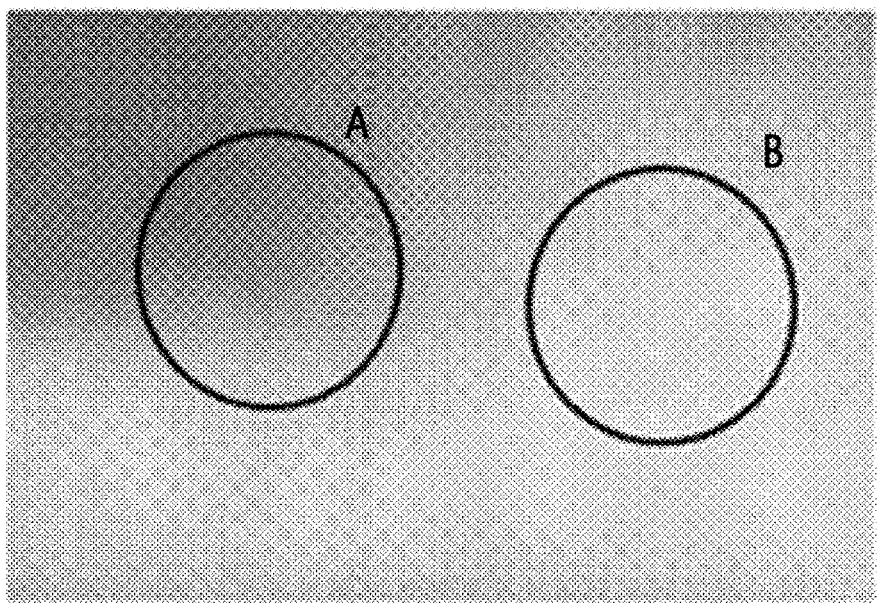

[FIG. 5]

| Reaction | Expression |
|---|---|
| Negative | - |
| Imperfection erythema | ± |
| Erythema | + |
| Small blister, Papule, Edema | ++ |
| Big blister, Necrosis | +++ |

METHOD FOR PREPARING FUNCTIONAL EXTRACT-CONTAINING POLYVINYL ALCOHOL FILM BY HETEROGENEOUS SAPONIFICATION OF POLYVINYL ACETATE FILM

RELATED APPLICATIONS

This application is the National Stage of International Patent Application No. PCT/KR2016/001963, filed Feb. 26, 2016, which is hereby incorporated by reference in its entirety, and which claims priority to Korean Patent Application No. 10-2015-0028140, filed Feb. 27, 2015.

TECHNICAL FIELD

The present invention relates to a method for preparing a functional extract-containing polyvinyl alcohol film with an improved specific surface area by having a wrinkled shape, and more specifically, to a method for preparing a functional extract-containing polyvinyl alcohol film having wrinkles formed on a surface thereof, including saponifying a functional extract-containing polyvinyl acetate film, while the functional extract-containing polyvinyl acetate film is immersed in a first solvent capable of maintaining the film form of the functional extract-containing polyvinyl acetate film, so as to convert the functional extract-containing polyvinyl acetate film into a functional extract-containing polyvinyl alcohol film.

BACKGROUND ART

The scientific name for Hoelen is *Poria cocos*, which taxonomically belongs to the Class Eubasidiomycetes, the Subclass Hymenomycetidae, the Order Aphyllophorales, and the Family Polyporaceae. *Poria cocos* is sclerotia that grow mainly in pine roots and is called differently according to its internal colors; e.g., white *Poria cocos* with a white internal color and red *Poria cocos* with the a internal color. Since ancient times, it has been said that *Poria cocos* keeps the spleen healthy, is used as an ataractic agent, has the effects of stabilizing atopic dermatitis and body warming. *Poria cocos* is effective for the treatment of peptic ulcer, muscle spasm, thirst, dizziness, mental anxiety, and insomnia. As a herbal medicine, *Poria cocos* has efficacies on stamina, diuresis, sedation, etc., and is thus used for the treatment of kidney disease, cystitis, and urethritis. Additionally, *Poria cocos* is known to have an inhibitory effect against contact dermatitis.

A *Poria cocos* extract not only has the effect of alleviating gastric dysfunction but also has the effect of boosting stamina. In herbal medicine, *Poria cocos* extracts are classified into sedatives and diuretics. Additionally, *Poria cocos* extracts are used as an important component in the preparation of herbal medicine for energy recovery. According to recent studies and experiments with regard to the pharmacological efficacy of *Poria cocos* extracts, *Poria cocos* extracts have excellent efficacy against tumor and can improve the immunities of people suffering from chronic diseases and protect the stomach and intestines.

*Sorghum bicolor* L. Moench (*Sorghum*) is an annual plant belonging to the Family of Gramineae, which is one of the important grains, and mainly consumed as food in Korea. *Sorghum* contains a large amount of functional ingredients such as dietary fibers, phenolic compounds, etc., and the phenolic compounds consist of flavonoids, tannins, phenolic acids, etc., and most of these are known as flavonoids. Recently, many studies on the physiological functions of *Sorghum* have been reported. *Sorghum* extracts are known to exhibit strong antioxidant activity. Studies on the functionality of *Sorghum* include a study confirming antioxidant and antimicrobial activity after sequential solvent fractionation of 25 kinds of *Sorghum* by methanol extraction, a study measuring antioxidant activity of *Sorghum* anthocyanin, and reports on the phenolic components contained in *Sorghum* such as phenolic acid, flavonoid, tannin, etc.

Polymer materials are new materials widely used from applications in everyday life such as food, clothing, and shelter to advanced engineering fields such as electronics, life science, nanotechnology, environmental science, etc. Polymer processing is essential in the preparation of the final products needed by humans using these materials. At present, polymer production is higher than steel production in the world, as well as in Korea and Japan. As the amount of polymer being used increases, the method of molding polymer products also has an important role. The main point in forming polymers is the selection of materials and product design to ensure quality satisfaction at competitive prices, mold design, and operation of molding machines. In particular, quality satisfaction may be regarded as one not only satisfying the requirements of the state or size of a surface but also having the mechanical property, the orientation of the molecule, the minimum residual stress, and the appropriate structure inside the materials. Furthermore, in addition to the rheological characteristics, it is also important to know whether the resin is crystalline, amorphous, and what the maximum crystallinity is when selecting resins for forming polymer products. This is because the design of the formed product through the forming process must be matched to the forming process and the subject material, and thus a sufficient understanding of the polymer forming method may be essential in designing an optimal product.

Among polymer processes, films are available for all applications where textiles and paper are used, and are used in all industrial fields including aerospace and electronics, display, food packaging, and agriculture.

Examples of the methods for producing films using a polymer may include a solution casting method in which a high-viscosity polymer solution obtained by dissolving a polymer in a solvent is developed on a wide, smooth, non-adhesive surface and the solvent is volatilized to obtain a film; a melt processing method in which a polymer material is melt-processed by heating to a melting temperature or softening temperature or higher using heat and pressure to obtain a film; etc. The melt processing method is disadvantageous in that the method is not suitable for high-quality films such as optical functional films because the melt processing method cannot precisely control the thickness of films, thus generating fine lines (so-called "die lines") on the films produced. In contrast, the solution casting method is advantageous in that the method can produce films with improved optical isotropy and thickness uniformity and fewer impurities compared to those prepared by the melt processing method. Additionally, the solution casting method is advantageous in that the method of use and installation equipment are very simple from the experimental aspect, and thus films with excellent properties can be easily produced according to the content of inorganic materials relative to various polymer materials.

Meanwhile, saponified polyvinyl alcohol has a relatively low viscosity compared to other polymers, is non-toxic, and has unique properties such as biodegradability. Additionally, saponified polyvinyl alcohol has excellent miscibility when blended with other polymers and is thus used for various purposes such as medical materials, packaging materials, release films, water-soluble films, etc. However, the methods of producing polyvinyl alcohol films reported so far have not been related to changing the surface of polyvinyl alcohol films, and in particular, there has been no report with regard to the method of controlling the surface roughness of polyvinyl alcohol films.

In this regard, for maximizing the specific surface area of polyvinyl alcohol films, the present inventors have made many efforts including controlling wrinkle formation or surface roughness of each polyvinyl alcohol film, and introducing the antioxidant effect or inhibitory effect against contact dermatitis of natural functional extracts such as a *Poria cocos* extract and *Sorghum* extract to the polyvinyl alcohol films in various ways. As a result, the present inventors have discovered that when a polyvinyl acetate film was prepared by the solution casting method using a natural functional extract and polyvinyl acetate as starting materials and then converted to polyvinyl alcohol containing the functional natural extract through a heterogeneous saponification process, the specific surface area of the film was improved while wrinkles were formed on the surface of the film and the film simultaneously contained the functional extract confirming the possibility of providing a functionality, thereby completing the present invention.

SUMMARY

An object of the present invention is to provide a polyvinyl alcohol film, which has an improved specific surface area due to the wrinkles formed on the surface thereof and a functionality of a functional extract simultaneously provided therein, and a method of preparing the polyvinyl alcohol film.

In order to achieve the above object, the present invention provides a method for preparing a functional extract-containing polyvinyl alcohol film having wrinkles formed on a surface thereof, including saponifying a functional extract-containing polyvinyl acetate film, while the functional extract-containing polyvinyl acetate film is immersed in a first solvent capable of maintaining the film form of the functional extract-containing polyvinyl acetate film, so as to convert the functional extract-containing polyvinyl acetate film into a functional extract-containing polyvinyl alcohol film.

Polyvinyl alcohol (PVA), which is a semi-crystalline synthetic polymer having a hydroxyl group capable of forming a hydrogen bond, cannot be synthesized by direct polymerization of vinyl alcohol monomers but is prepared by synthesis of polyvinyl acetate (PVAc) using vinyl acetate-based monomers followed by hydrolysis of polyvinyl acetate (PVAc) with an alkali or acid. Polyvinyl acetate and polyvinyl alcohol differ in the types of solvents in which they can be dissolved. Specifically, polyvinyl acetate can be dissolved in methanol, ethanol, tetrahydrofuran (THF), dimethyl sulfoxide (DMSO), benzene, acetone, ethyl acetate, methylene chloride, methylethylketone, toluene, ethylene glycol diacetate, etc., but is hardly dissolved in water. Additionally, polyvinyl alcohol is soluble in water but is hardly dissolved in organic solvents. Natural functional extracts can be obtained by using a variety of extraction solvents and the extraction solvent may vary depending on the type of functional ingredients. Accordingly, when the film is prepared by dissolving polyvinyl alcohol in a solvent to prepare a polymer solution followed by forming into a film, the natural functional extract using an organic solvent as an extraction solvent may be difficult to prepare into a uniform polymer solution together with polyvinyl alcohol.

In the present invention, a functional extract-containing polyvinyl alcohol film is prepared through the method of heterogeneous saponification after dissolving the functional extract together with polyvinyl acetate and preparing into a film. Accordingly, the present invention is advantageous in that a polyvinyl alcohol film, in which the functional extract using an organic solvent as the extraction solvent is more uniformly contained, can be prepared. Additionally, even in the case of a functional extract using water as an extraction solvent, the functional extract can be prepared into a polymer solution together with polyvinyl acetate which is soluble in alcohols such as methanol, ethanol, etc. Therefore, the present invention can produce a polyvinyl alcohol film in which functional extracts obtained by using a variety of extraction solvents are uniformly contained.

Furthermore, the method of preparing a functional extract-containing polyvinyl alcohol film according to the present invention can prepare a functional extract-containing polyvinyl alcohol film, which has a novel structure with an improved specific surface area compared to that of the polyvinyl alcohol film having a smooth surface, by having a wrinkled form on a surface thereof, and the film may exhibit more improved effects by application to implants, synthetic fibers, packaging materials, coating agents, adhesive agents, polarizing films, etc.

In the present invention, the functional extract-containing polyvinyl acetate film may be prepared by forming a polymer solution, in which a functional extract and polyvinyl acetate are dissolved in a second solvent, followed by drying. Specifically, the high-viscosity polymer solution obtained by dissolving a functional extract and polyvinyl acetate in the second solvent may be prepared by a solution casting method (solvent casting method), in which the high-viscosity polymer solution is developed on a wide, smooth, non-adhesive surface and the solvent is volatilized in the second solvent to obtain a film.

As used herein, the term "functional extract" refers to a functional material obtained by extracting at least one natural product or at least one composite obtained by synthesizing at least one natural product component. The functional extract may include the extracts themselves and all of the formulations that may be formed using the extracts, such as a liquid extract obtained by extraction treatment, a diluent or concentrate of the liquid extract, a dry product obtained by drying the liquid extract, or a crude purified product or purified product of the liquid extract, a mixture thereof, etc.

In the present invention, the raw material to be used for the natural functional extract may include Hoelen, *Sorghum, Houttuyniae cordata, Persicae semen, Persicae semen* shell, *Isatidis radix, rigida, Taraxacum* herb, *Dictyophora indusiata, Coriolus versicolor, Ganoderma lucidum, Magnoliae flos, Taraxacum platycarpum*, chestnut inner shell, *Camellia* oil, phytoncide, willow, birch, pine, Japanese elm, *Spiraea prunifolia, Alibizzia julibrissin*, potato, licorice, *Sophora flavescens*, brown algae, guar gum, oyster, grape seeds, honey, green tea, carrot, *Swertia japonica* MAKINO, *Chrysanthemum*, strawberry, rosemary, locust bean gum, *Macadamia* nut oil, *Matricaria*, starch, *Bifidus*, safflower oil, *Mori cortex radicis*, sage, Luffa, plant squalene, silk, acacia, rice, Japanese mugwort, almond, avocado, ivy, aloe, corn, olive, milk protein, *Curcuma*, soluble licorice, *ginseng, Paeonia lactiflora*, rose, *Acorus calamus, Cnidium officinale, Gardenia*, coconut, parsley, henna, horsetail, Jojoba, loess, dimethyl sulfone, grape seeds, pomegranate, β-carotene, vitamins, herbs, ginger, *Kochia scoparia, Lycium chinense,*

*Lithospermum erythrorhizon, Nelumbo nucifera* leaves, a composite thereof, or a mixture of at least one thereof. In Preparation Examples, Examples, and Experimental Examples of the present invention, a mixture (1:1, w/w) of a methanol extract of Hoelen and a methanol extract *Sorghum* was used. The mixture of the methanol extract of Hoelen and methanol extract *Sorghum* is called a natural functional extract or functional extract, being limited to the above-mentioned Preparation Examples, Examples, and Experimental Examples.

The scientific name for Hoelen is *Poria cocos*, which taxonomically belongs to the Class Eubasidiomycetes, the Subclass Hymenomycetidae, the Order Aphyllophorales, and the Family Polyporaceae. *Poria cocos* is sclerotia that grow mainly in pine roots and is called differently according to its internal color; e.g., white *Poria cocos* with a white internal color and red *Poria cocos* with a red internal color. Since ancient times, it has been said that *Poria cocos* keeps the spleen healthy, is used as an ataractic agent, has the effects of stabilizing atopic dermatitis and body warming. *Poria cocos* is effective for the treatment of peptic ulcer, muscle spasm, thirst, dizziness, mental anxiety, and insomnia. As a herbal medicine, *Poria cocos* has efficacies on stamina, diuresis, sedation, etc., and is thus used for the treatment of kidney disease, cystitis, and urethritis. Additionally, *Poria cocos* is known to have an inhibitory effect against contact dermatitis.

A *Poria cocos* extract not only has the effect of alleviating gastric dysfunction but also has the effect of boosting stamina. In herbal medicine, *Poria cocos* extracts are classified into sedatives and diuretics. Additionally, *Poria cocos* extracts are used as an important component in the preparation of herbal medicine for energy recovery. According to recent studies and experiments with regard to the pharmacological efficacy of *Poria cocos* extracts, *Poria cocos* extracts have excellent efficacy against tumor and can improve the immunities of people suffering from chronic diseases and protect the stomach and intestines.

*Sorghum bicolor* L. Moench (*Sorghum*) is an annual plant belonging to the Family of Gramineae, which is one of the important grains, and mainly consumed as food in Korea. *Sorghum* contains a large amount of functional ingredients such as dietary fibers, phenolic compounds, etc., and the phenolic compounds consist of flavonoids, tannins, phenolic acids, etc., and most of these are known as flavonoids. Recently, many studies on the physiological functions of *Sorghum* have been reported. *Sorghum* extracts are known to exhibit strong antioxidant activity. Studies on the functionality of *Sorghum* include a study confirming antioxidant and antimicrobial activity after sequential solvent fractionation of 25 kinds of *Sorghum* by methanol extraction, a study measuring antioxidant activity of *Sorghum* anthocyanin, and reports on the phenolic components contained in *Sorghum* such as phenolic acid, flavonoid, tannin, etc.

The functional extract of the present invention may be extracted from natural, hybrid, or variant plants of each corresponding plant and may also be extracted from plant tissue cultures and their composites.

With regard to the extraction of the functional extract of the present invention, the extraction method is not particularly limited and the extraction may be performed according to a conventional method used in the art. Non-limiting examples of the extraction method include a hot water extraction method, an ultrasonic extraction method, a filtration method, a reflux extraction method, etc., and these methods may be performed alone or in any combination of two or more thereof.

In the present invention, the kind of the extraction solvent used for extracting the functional extract may be variously selected, including water and organic solvents as described above, and preferably a solvent capable of dissolving polyvinyl acetate, i.e., those which are the same as or are soluble and/or miscible with the second solvent. Non-limiting examples of the extraction solvent may include water; $C_{1-4}$ lower alcohols such as methanol, ethanol, propyl alcohol, butyl alcohol, etc.; polyhydric alcohols such as glycerin, butylene glycol, propylene glycol, etc.; hydrocarbon solvents such as methyl acetate, ethyl acetate, acetone, benzene, hexane, diethyl ether, dichloromethane, etc.; or a mixture thereof. Preferably, water, a lower alcohol, a polyhydric alcohol, or a hydrocarbon-based solvent may be used alone or in combination of two or more thereof. More preferably, the extraction solvent may be the same as the second solvent. When the extraction solvent and the second solvent are the same, the extraction solvent containing the functional extract can be used without any treatment. Additionally, the polyvinyl acetate can be dissolved using the solvent used as the extraction solvent, and thus the second solvent can be saved. Furthermore, unnecessary interaction between the extraction solvent and the second solvent does not occur and thus the reaction efficiency can be improved.

In the present invention, the extract obtained by heat extraction or cold extraction may be used after filtration to remove suspended solid particles. For example, the particles may be filtered using nylon, etc., or filtered by freezing filtration, etc., and used as they are or used after drying the filtrate by spray drying, etc.

In the present invention, the concentration of the functional extract in the polymer solution may be in a range of 0.05 wt % to 10 wt %. When the concentration is less than 0.05 wt %, it may be difficult to exhibit the functionality of the functional extract. In contrast, when the concentration exceeds 10 wt %, the amount of the functional extract is too large to control the viscosity of the polymer solution and the dispersion of the functional extract, thus making it difficult to form a film, and also there is a problem in that the functional extract is not uniformly distributed in the prepared film.

In the present invention, polyvinyl acetate may be prepared for use by bulk polymerization, solution polymerization, emulsion polymerization, and suspension polymerization methods. In particular, the bulk polymerization is advantageous in that polyvinyl acetate having a relatively high molecular weight can be obtained because the probability of chain transfer is lower than that of other polymerization methods because only monomers are present in the polymerization system.

In the present invention, the second solvent is not limited as long as it is a solvent capable of dissolving polyvinyl acetate, and preferably, methanol, ethanol, tetrahydrofuran (THF), dimethyl sulfoxide (DMSO), benzene, acetone, ethyl acetate, methylene chloride, methylethylketone, toluene, ethylene glycol diacetate, or a solvent mixture thereof.

The concentration of polyvinyl acetate in the polymer solution, as a factor related to the viscosity of the polymer solution, may be in a range of 1 wt % to 30 wt %. When the concentration of polyvinyl acetate is less than 1 wt %, the solution is too thin to form a film, and when it exceeds 30 wt %, it is difficult to form a film due to high viscosity. More preferably, when the concentration of polyvinyl acetate in the polymer solution is 6 wt % to 15 wt %, and most preferably 8 wt % to 10 wt %, the film can be easily formed due to an appropriate viscosity of the polymer solution.

The functional extract and polyvinyl acetate may be dissolved in a shaking water bath at a temperature of 30° C. to 50° C. for 0.1 hour to 5 hours, and preferably at 40° C. for 30 minutes. When the temperature is outside the range, the natural functional extract and/or polyvinyl acetate may not be completely dissolved, and thus there is a problem in that a uniform film may not be formed. Additionally, the manufacturing method according to the present invention can stabilize the polymer solution by allowing the solution to stand at room temperature of 20° C. to 35° C. for 0.5 hours to 5 hours, and preferably, at 20° C. for 1 hour.

Thereafter, the polymer solution is developed on the surface of a smooth non-adhesive substrate and the solvent is volatilized to produce a film. A vacuum dryer may be used to volatilize the solvent, and a natural functional extract-containing polyvinyl acetate film placed on a flat surface can be obtained by setting the external vapor pressure at 10 cmHg to 76 cmHg and volatilizing the solvent at a temperature of about 30° C. to about 50° C. for 24 hours to 60 hours, and more preferably, at an external vapor pressure of 35 cmHg and for a drying time of 48 hours.

When the external vapor pressure is less than 10 cmHg, there is a problem in that the external vapor pressure for volatilizing the solvent is small and thus the volatilization rate of the solvent is low. In contrast, when the external vapor pressure exceeds 76 cmHg, the volatilization rate of the solvent is high, but there is a problem in that holes are formed on the surface of the film.

When the drying time is less than 24 hours, there is a problem in that the time for volatilizing the solvent is insufficient and thus a film may not be formed.

In particular, the film is collected in the form of a film having a two-dimensional structure by producing using a conventional solution casting apparatus.

Specifically, the conventional solution casting apparatus consists of a vacuum dryer, a vapor pressure injector, and cold traps as shown in FIG. 1

A functional extract-containing polyvinyl alcohol film having wrinkles formed on a surface thereof can be prepared by converting a functional extract-containing polyvinyl acetate film into a functional extract-containing polyvinyl alcohol film via saponification of the functional extract-containing polyvinyl acetate film, while the functional extract-containing polyvinyl acetate film is immersed in a solvent capable of maintaining the film form of the functional extract-containing polyvinyl acetate film (i.e., a first solvent).

The preparation method of the present invention is not a process of saponifying a functional extract and polyvinyl acetate in a second solvent but saponifying a functional extract-containing polyvinyl acetate film upon preparation while maintaining the film form, and surprisingly, a functional extract-containing polyvinyl alcohol film having wrinkles formed on a surface thereof is formed. Accordingly, it is important to use the first solvent that can maintain the form of the functional extract-containing polyvinyl acetate film during saponification.

Specifically, the functional extract-containing polyvinyl alcohol film may be prepared by immersing the functional extract-containing polyvinyl acetate film to the first solvent, thereby converting the —OCOCH$_3$ group of the polyvinyl acetate film into a —OH group by heterogeneous saponification.

In the present invention, the first solvent may be an acid solution or alkali solution, which includes a dispersant and a swelling agent. The dispersant and the swelling agent act as catalysts to cause heterogeneous surface saponification by saponifying only the surface while maintaining the film form of the functional extract-containing polyvinyl acetate film.

The acid in the acid solution for the saponification may be hydrochloric acid, nitric acid, sulfuric acid, or a mixture thereof and the alkali in the alkali solution for the saponification may be sodium chloride, sodium hydroxide, potassium hydroxide, sodium bromide, sodium iodide, or a mixture thereof, but the acid solution and the alkali solution are not limited thereto.

The dispersant may be sodium sulfate, sodium sulfite, calcium sulfate, magnesium sulfate, or a mixture thereof.

Additionally, the swelling agent may be methanol, ethanol, propanol, ethylene glycol, propylene glycol, tetrahydrofuran (THF), dimethyl sulfoxide (DMSO), benzene, acetone, or a mixture thereof. Preferably, methanol, which is easy to obtain, low in cost, easy to handle, and has a low boiling point, is used.

The acid solution may be one which is prepared by dissolving after mixing any one selected from hydrochloric acid, nitric acid, sulfuric acid, or a mixture thereof; any one dispersant selected from sodium sulfate, sodium sulfite, calcium sulfate, magnesium sulfate, or a mixture thereof; any one swelling agent selected from methanol, ethanol, propanol, ethylene glycol, propylene glycol, tetrahydrofuran (THF), dimethyl sulfoxide (DMSO), benzene, acetone, or a mixture thereof; and water, preferably distilled water, but the acid solution is not limited thereto.

More preferably, the acid solution may be one which is prepared by dissolving after mixing any one selected from hydrochloric acid, nitric acid, sulfuric acid, or a mixture thereof in an amount of 1 g to 30 g; any one dispersant selected from sodium sulfate, sodium sulfite, calcium sulfate, magnesium sulfate, or a mixture thereof in an amount of 1 g to 30 g; any one swelling agent selected from methanol, ethanol, propanol, ethylene glycol, propylene glycol, tetrahydrofuran (THF), dimethyl sulfoxide (DMSO), benzene, acetone, or a mixture thereof in an amount of 1 g to 30 g; and water in an amount of 10 mL to 500 mL, based on 1 g of the functional extract-containing polyvinyl acetate film, respectively.

The alkali solution may be one which is prepared by dissolving after mixing any one selected from sodium chloride, sodium hydroxide, potassium hydroxide, sodium bromide, sodium iodide, or a mixture thereof; any one dispersant selected from sodium sulfate, sodium sulfite, calcium sulfate, magnesium sulfate, or a mixture thereof; any one swelling agent selected from methanol, ethanol, propanol, ethylene glycol, propylene glycol, tetrahydrofuran (THF), dimethyl sulfoxide (DMSO), benzene, acetone, or a mixture thereof; and water, preferably distilled water, but the acid solution is not limited thereto.

More preferably, the alkali solution may be one which is prepared by dissolving after mixing any one selected from sodium chloride, sodium hydroxide, potassium hydroxide, sodium bromide, sodium iodide, or a mixture thereof in an amount of 1 g to 30 g; any one dispersant selected from sodium sulfate, sodium sulfite, calcium sulfate, magnesium sulfate, or a mixture thereof in an amount of 1 g to 30 g; any one swelling agent selected from methanol, ethanol, propanol, ethylene glycol, propylene glycol, tetrahydrofuran (THF), dimethyl sulfoxide (DMSO), benzene, acetone, or a mixture thereof in an amount of 1 g to 30 g; and water in an amount of 10 mL to 500 mL, based on 1 g of the functional extract-containing polyvinyl acetate film, respectively.

More specifically, the alkali solution may be one which is prepared by dissolving after mixing sodium chloride; sodium sulfate; methanol; and water, preferably distilled water, but the alkali solution is not limited thereto.

When the kind and amount of the acid solution or the alkali solution are not satisfied, it may not be easy to form wrinkles on the surface of the film while the —OCOCH$_3$ group is converted into a —OH group.

In the present invention, the degree of saponification is preferably in the range of 60% to 99.9%. As used herein, the term "degree of saponification" refers to the rate of the units actually saponified into vinyl alcohol units among the units obtained by conversion to vinyl alcohol units by saponification, and may be measured by the method described in JIS. Specifically, degree of saponification may be expressed as a ratio of the number of moles between the total number of moles of the compound converted to the —OH groups and the number of moles of the compound having the —OCOCH$_3$ groups.

In the present invention, the saponification of the natural functional extract-containing polyvinyl acetate film may be performed at a temperature of 5° C. to 80° C. for 10 hours to 300 hours, preferably at 40° C. to 50° C. for 30 hours to 150 hours, and most preferably at 50° C. for 150 hours.

The purpose of performing the saponification at a temperature of 5° C. to 80° C. is to maximize the activation of a swelling agent (e.g., methanol) acting as a catalyst. Methanol has a boiling point of about 64.7° C., and thus methanol evaporates when heated above the temperature. When saponification is performed at a temperature below 5° C., the saponification degree becomes about 50% and the saponification degree at 50° C. may reach 99.9%. In the present invention, unless the saponification temperature exceeds the boiling point of the swelling agent, a functional extract-containing polyvinyl alcohol film having a saponification degree of 99.9% is formed even when the temperature for saponification is raised to 80° C.

Additionally, the purpose of performing the saponification for 10 hours to 300 hours is to prepare a natural functional extract-containing polyvinyl alcohol film having a saponification degree of 60% to 99.9%. As the time for introducing the natural functional extract polyvinyl acetate film into a first solvent becomes longer, the conversion of —OCOCH$_3$ groups into —OH groups may become higher. When the saponification is performed for less than 10 hours the saponification degree becomes about 30%, and thus, the saponification time is insufficient for achieving the saponification degree of 60% to 99.9%. Additionally, when the saponification is performed for at least 150 hours, the functional extract-containing polyvinyl alcohol film having a saponification degree of 99.9% can be produced. Accordingly, even when the saponification is performed for more than 150 hours, the natural functional extract-containing polyvinyl alcohol film having a saponification degree of 99.9% can be produced. However, performing the saponification in excess of 300 hours is not economical.

Another aspect of the present invention provides a functional extract-containing polyvinyl alcohol film having wrinkles formed on a surface thereof.

The wrinkles of the natural functional extract-containing polyvinyl alcohol film may be formed to have a depth of 10 nm to 10 μm. When the depth of the wrinkles of the polyvinyl alcohol film is less than 10 nm, the effect of increasing the specific surface area of the polyvinyl alcohol film due to wrinkles formed on the surface is negligible. In contrast, when the depth of the wrinkles of the polyvinyl alcohol film exceeds 10 μm, cracks are generated in the polyvinyl alcohol film, which is disadvantageous in film formation.

The functional extract-containing polyvinyl alcohol film on which wrinkles are formed on the surface of the film of the present invention may be produced by the preparation method according to the present invention. Unlike the conventional polyvinyl alcohol films which are prepared to have a smooth surface, the functional extract-containing polyvinyl alcohol film prepared by heterogeneous saponification according to the present invention has uneven wrinkles formed on the surface of the film, being folded many times without directionality, thereby being capable of maximizing the specific surface area of the film. Accordingly, the amount of the functional extract can be increased to the polyvinyl alcohol film, and also, the area to be in contact with the material contacting the film can be increased, and thus the functional extract-containing polyvinyl alcohol film can have beneficial effects with respect to interactions such as contact strength, material transfer, etc.

The functional extract-containing polyvinyl alcohol film with a novel form, in which wrinkles are formed on the film, has improved specific surface area and is thus expected to be applicable to various fields including implants, synthetic fibers, packaging materials, coating agents, adhesive agents, polarizing films, etc., thereby exhibiting more excellent properties.

Additionally, the prepared functional extract-containing polyvinyl alcohol film can be provided with the functionality of natural extracts such as an antioxidant effect, an inhibitory effect against contact dermatitis, etc.

Advantageous Effects of the Invention

According to the preparation method of the present invention, a novel polyvinyl alcohol film which has an improved specific surface area and is simultaneously provided with a functionality of a functional extract, compared to the conventional polyvinyl alcohol films, by having wrinkles formed on a surface of the polyvinyl alcohol film can be prepared.

BRIEF DESCRIPTION OF DRAWINGS

FIG. 1 shows an image of a solution casting device of the present invention.

FIG. 2 shows optical microscope images of a heterogeneously-saponified polyvinyl alcohol film prepared according to the amount of an alkali solution. The saponification temperature (50° C.) and saponification time (120 hours) used were the same.
(a) NaOH (5 g), Na$_2$SO$_4$ (5 g), and MeOH (5 g)
(b) NaOH (10 g), Na$_2$SO$_4$ (10 g), and MeOH (10 g)

FIG. 3 shows optical microscope images of a heterogeneously-saponified polyvinyl alcohol film prepared according to the saponification time. The alkali solutions necessary for the saponification [NaOH (10 g), Na$_2$SO$_4$ (10 g), and MeOH (10 g)] and the saponification temperature (50° C.) used were the same.
(a) saponification time (90 hours)
(b) saponification time (150 hours)

FIG. 4 shows an image of an experiment result with regard to skin safety evaluation, in which the prepared natural functional extract-containing polyvinyl alcohol film was applied to skin.

FIG. 5 shows a table illustrating criteria for the judgment of the International Society for Contact Dermatology.

DETAILED DESCRIPTION OF THE INVENTION

Hereinafter, the present invention will be described in more detail with reference to the following Examples. However, these Examples are for illustrative purposes only and the invention is not intended to be limited by these Examples. Among the compounds used below, the starting materials and reagents were purchased from Aldrich and all solvents were used without drying or purification because they were pure.

In the following Preparation Examples 1 to 4, experiments for the preparation of natural functional extract-containing polyvinyl acetate films were performed. A polyvinyl acetate film in an optimum condition was prepared from a natural functional extract-containing polyvinyl acetate solution dissolved in methanol by solvent volatilization. In particular, a mixture (1:1, w/w) of a methanol extract of Hoelen and a methanol extract *Sorghum* was used as a functional extract, and it is called a natural functional extract being limited to Preparation Examples, Examples, and Experimental Examples of the present invention.

Preparation Example 1: Preparation of Natural Functional Extract-Containing Polyvinyl Acetate Film Polyvinyl acetate (4 wt %) was added to a 99% pure methanol solvent (37.92 mL), stirred at 40° C. for 30 minutes, stabilized for 1 hour, and 1 wt % of a natural functional extract was added to the solution and stirred at 40° C. for 30 min. The prepared polyvinyl acetate solution was dried at room temperature for about one hour, evenly spread over the entire stainless steel box (10 cm×10 cm), and the solvent was volatilized in a 40° C. vacuum dryer for 48 hours to prepare a natural functional extract-containing polyvinyl acetate film.

Preparation Example 2: Preparation of Natural Functional Extract-Containing Polyvinyl Acetate Film A natural functional extract-containing polyvinyl acetate film was prepared in the same manner as in Preparation Example 1 except that the concentration of polyvinyl acetate was adjusted to 6 wt %.

Preparation Example 3: Preparation of Natural Functional Extract-Containing Polyvinyl Acetate Film A natural functional extract-containing polyvinyl acetate film was prepared in the same manner as in Preparation Example 1 except that the concentration of polyvinyl acetate was adjusted to 8 wt %.

Preparation Example 4: Preparation of Natural Functional Extract-Containing Polyvinyl Acetate Film A natural functional extract-containing polyvinyl acetate film was prepared in the same manner as in Preparation Example 1 except that the concentration of polyvinyl acetate was adjusted to 10 wt %.

The conditions and results of Preparation Examples 1 to 4 are summarized in Table 1 below.

In the following Examples 1 to 4, experiments were performed to prepare a natural functional extract-containing polyvinyl alcohol film by saponification of the natural functional extract-containing polyvinyl acetate film prepared in Preparation Example 3. After performing saponification of the natural functional extract-containing polyvinyl acetate film prepared in Preparation Example 3 using an alkali solution, the saponified film was put into distilled water, stirred again, and dried at room temperature to obtain a natural functional extract-containing polyvinyl alcohol film.

Example 1: Preparation of Natural Functional Extract-Containing Polyvinyl Alcohol Film Via Heterogeneous Saponification of Natural Functional Extract-Containing Polyvinyl Acetate Film For the saponification process of a natural functional extract-containing polyvinyl acetate film prepared by the solution casting method, distilled water (100 mL), NaOH (10 g), $Na_2SO_4$ (10 g), and MeOH (10 g), based on 1 g of the natural functional extract-containing polyvinyl acetate film, were gently stirred to prepare an alkali solution. The prepared natural functional extract-containing polyvinyl acetate film was added to the prepared alkali solution and the saponification was performed at 50° C. for 30 hours. After the saponification, the film was washed several times with distilled water, and the washed film was dried at room temperature for 12 hours to prepare a saponified natural functional extract-containing polyvinyl alcohol film. In Examples 2 to 15 below, a natural functional extract-containing polyvinyl alcohol film was prepared by changing the saponification conditions according to Table 2.

Example 2: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 50° C. for 60 hours after putting a natural functional extract-containing polyvinyl acetate film into the prepared alkali solution.

Example 3: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in

TABLE 1

| Category | Polymer Used | Polymer Conc. | Natural Functional Extract Conc. | Temp. | Vapor Pressure | Drying Time | Film Formation |
| --- | --- | --- | --- | --- | --- | --- | --- |
| Prep. Ex. 1 | Polyvinyl Acetate (PVAc) | 4 wt % | 1 wt % | 40° C. | 35 cmHg | 48 hours | x |
| Prep. Ex. 2 | Polyvinyl Acetate (PVAc) | 6 wt % | 1 wt % | 40° C. | 35 cmHg | 48 hours | x |
| Prep. Ex. 3 | Polyvinyl Acetate (PVAc) | 8 wt % | 1 wt % | 40° C. | 35 cmHg | 48 hours | o |
| Prep. Ex. 4 | Polyvinyl Acetate (PVAc) | 10 wt % | 1 wt % | 40° C. | 35 cmHg | 48 hours | o |

Example 1 except that saponification was performed at 50° C. for 90 hours after putting a natural functional extract-containing polyvinyl acetate film into the prepared alkali solution.

Example 4: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 50° C. for 120 hours after putting a natural functional extract-containing polyvinyl acetate film into the prepared alkali solution.

Example 5: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 50° C. for 150 hours after putting a natural functional extract-containing polyvinyl acetate film into the prepared alkali solution.

Example 6: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that an alkali solution prepared using distilled water (50 mL), NaOH (5 g), $Na_2SO_4$ (5 g), and MeOH (5 g) was used.

Example 7: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 6 except that saponification was performed at 50° C. for 60 hours after putting a natural functional extract-containing polyvinyl acetate film into the prepared alkali solution.

Example 8: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 6 except that saponification was performed at 50° C. for 90 hours after putting a natural functional extract-containing polyvinyl acetate film into the prepared alkali solution.

Example 9: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 6 except that saponification was performed at 50° C. for 120 hours after putting a natural functional extract-containing polyvinyl acetate film into the prepared alkali solution.

Example 10: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 6 except that saponification was performed at 50° C. for 150 hours after putting a natural functional extract-containing polyvinyl acetate film into the prepared alkali solution.

Example 11: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 40° C. for 30 hours after putting a natural functional extract-containing polyvinyl acetate film into the prepared alkali solution.

Example 12: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 40° C. for 60 hours after putting a natural functional extract-containing polyvinyl acetate film into the prepared alkali solution.

Example 13: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 40° C. for 90 hours after putting a natural functional extract-containing polyvinyl acetate film into the prepared alkali solution.

Example 14: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 40° C. for 120 hours after putting a natural functional extract-containing polyvinyl acetate film into the prepared alkali solution.

Example 15: Preparation of Natural Functional Extract-Containing Polyvinyl Alcohol Film Via Heterogeneous Saponification of Natural Functional Extract-Containing Polyvinyl Acetate Film A saponified natural functional extract-containing polyvinyl alcohol film was prepared in the same manner as in Example 1 except that saponification was performed at 40°

C. for 150 hours after putting a natural functional extract-containing polyvinyl acetate film into the prepared alkali solution.

The conditions and results of Examples 1 to 15 are summarized in Table 2 below.

polyvinyl alcohol film prepared according to the saponification time. The alkali solutions necessary for the saponification [NaOH (10 g), Na$_2$SO$_4$ (10 g), and MeOH (10 g)] and the saponification temperature (50° C.) used were the same.

TABLE 2

| Category | Distilled Water | Alkali Solution | | | Saponification Reaction | |
| | | NaOH | Na$_2$SO$_4$ | MeOH | Temperature | Time |
| --- | --- | --- | --- | --- | --- | --- |
| Example 1 | 100 mL | 10 g | 10 g | 10 g | 50° C. | 30 hours |
| Example 2 | 100 mL | 10 g | 10 g | 10 g | 50° C. | 60 hours |
| Example 3 | 100 mL | 10 g | 10 g | 10 g | 50° C. | 90 hours |
| Example 4 | 100 mL | 10 g | 10 g | 10 g | 50° C. | 120 hours |
| Example 5 | 100 mL | 10 g | 10 g | 10 g | 50° C. | 150 hours |
| Example 6 | 50 mL | 5 g | 5 g | 5 g | 50° C. | 30 hours |
| Example 7 | 50 mL | 5 g | 5 g | 5 g | 50° C. | 60 hours |
| Example 8 | 50 mL | 5 g | 5 g | 5 g | 50° C. | 90 hours |
| Example 9 | 50 mL | 5 g | 5 g | 5 g | 50° C. | 120 hours |
| Example 10 | 50 mL | 5 g | 5 g | 5 g | 50° C. | 150 hours |
| Example 11 | 100 mL | 10 g | 10 g | 10 g | 40° C. | 30 hours |
| Example 12 | 100 mL | 10 g | 10 g | 10 g | 40° C. | 60 hours |
| Example 13 | 100 mL | 10 g | 10 g | 10 g | 40° C. | 90 hours |
| Example 14 | 100 mL | 10 g | 10 g | 10 g | 40° C. | 120 hours |
| Example 15 | 100 mL | 10 g | 10 g | 10 g | 40° C. | 150 hours |

Through the above experiments, it was confirmed that in the case of the natural functional extract-containing polyvinyl alcohol film, which was prepared by heterogeneous saponification performed at a temperature of 40° C. to 50° C. for a saponification time of 30 hours to 150 hours by adding into an alkali solution containing distilled water (950 mL to 100 mL), NaOH (5 g to 10 g), Na$_2$SO$_4$ (5 g to 10 g), and MeOH (5 g to 10 g), a natural functional extract-containing polyvinyl alcohol film having a saponification degree of 60% to 99.9% was formed. In particular, it was confirmed that in the case of the natural functional extract-containing polyvinyl alcohol film, which was prepared by heterogeneous saponification performed at 50° C. for a saponification time of 150 hours by adding into a mixed alkali solution containing distilled water (100 mL), NaOH (10 g), Na$_2$SO$_4$ (10 g), and MeOH (10 g), a natural functional extract-containing polyvinyl alcohol film having a saponification degree of 99.9% was formed.

As Experimental Examples to support the effect of the present invention, Experimental Example 1 relates to the analysis of the surface shape of the natural functional extract-containing polyvinyl alcohol film, and Experimental Example 2 relates to the functional analysis of the natural functional extract-containing polyvinyl alcohol film. Further details are given in Experimental Examples 1 and 2 below.

Experimental Example 1: Surface Shape Analysis of Natural Functional Extract-Containing Polyvinyl Alcohol Film The surface shape of the natural functional extract-containing polyvinyl alcohol film according to the amount of an alkali solution and saponification time was analyzed. The results are shown in FIGS. 2 and 3.

FIG. 2 shows confocal microscope images of a heterogeneously-saponified, natural functional extract-containing polyvinyl alcohol film prepared according to the amount of an alkali solution. The saponification temperature (50° C.) and saponification time (120 hours) used were the same.
(a) NaOH (5 g), Na$_2$SO$_4$ (5 g), and MeOH (5 g)
(b) NaOH (10 g), Na$_2$SO$_4$ (10 g), and MeOH (10 g)

FIG. 3 shows confocal microscope images of a heterogeneously-saponified, natural functional extract-containing (a) saponification time (90 hours)
(b) saponification time (150 hours)

From FIGS. 2 and 3, it can be confirmed that the functional extract-containing polyvinyl alcohol film of the present invention has uneven wrinkles formed on the surface of the film, being folded many times without directionality, and thus the specific surface area of the film was maximized.

Experimental Example 2: Functionality Analysis of Natural Functional Extract-Containing Polyvinyl Alcohol Film FIG. 4 shows an image of an experiment with regard to skin-safety evaluation, in which the prepared natural functional extract-containing polyvinyl alcohol film was applied to skin; and FIG. 5 shows a table illustrating criteria for the determination of the International Society for Contact Dermatology.

A skin-safety evaluation patch test was performed by applying the natural functional extract-containing polyvinyl alcohol film prepared in Example 1 above to the skin. The safety evaluation test was performed using a conventional polyvinyl alcohol film (a) and a natural functional extract-containing polyvinyl alcohol film (b), which were stored at room temperature for 2 weeks, via sealed-application to a region of the skin inside the arm using the Finn chamber on scanpor tape and the reaction on the skin was confirmed by the naked eye. The safety evaluation was determined according to the Criteria of Determination of the International Society for Contact Dermatology. For the natural functional extract, a *Poria cocos* extract and a *Sorghum* extract were used as described above. Referring to FIGS. 4 and 5, it was confirmed that when the polyvinyl alcohol film containing the *Poria cocos* extract and *Sorghum* extract was prepared and applied to the skin to perform a patch test for the purpose of skin-safety evaluation, no skin troubles occurred and contact dermatitis was not induced. Additionally, it was confirmed that the patch test did not induce any skin irritation with regard to skin safety.

In the case of applying via a patch the conventional polyvinyl alcohol film (a) in a sealed condition for 24 hours, the aeration was blocked and the skin is erythema. In contrast, in case of applying via a patch the natural functional extract-containing polyvinyl alcohol film (b), which is a polyvinyl alcohol film containing the *Poria cocos* extract and *Sorghum* extract, no erythema was observed because the polyvinyl alcohol film has many wrinkles and thus provided functionalities (antibacterial and antioxidant properties) to the area where the film is in contact with the skin.

The invention claimed is:

1. A method for preparing a functional extract or chemical compound-containing polyvinyl alcohol film having wrinkles formed on a surface thereof, comprising saponifying a functional extract or chemical compound-containing polyvinyl acetate film, while the functional extract or chemical compound-containing polyvinyl acetate film is immersed in a first solvent capable of maintaining the film form of the functional extract or chemical compound-containing polyvinyl acetate film, so as to convert the functional extract or chemical compound-containing polyvinyl acetate film into a functional extract or chemical compound-containing polyvinyl alcohol film.

2. The method of claim 1, wherein the functional extract or chemical compound-containing polyvinyl acetate film is prepared by forming a polymer solution, in which a functional extract or chemical compound and polyvinyl acetate are dissolved in a second solvent followed by drying.

3. The method of claim 2, wherein the functional extract is obtained using the same solvent as the second solvent as an extraction solvent.

4. The method of claim 2, wherein the functional extract is an extract of Hoelen, *Sorghum, Houttuyniae cordata, Persicae semen, Persicae semen* shell, *Isatidis radix, rigida, Taraxacum* herb, *Dictyophora indusiata, Coriolus versicolor, Ganoderma lucidum, Magnoliae flos, Taraxacum platycarpum*, chestnut inner shell, *Camellia* oil, phytoncide, willow, birch, pine, Japanese elm, *Spiraea prunifolia, Alibizzia julibrissin*, potato, licorice, *Sophora flavescens*, brown algae, oyster, grape seeds, honey, green tea, carrot, *Swertia japonica* MAKINO, *Chrysanthemum*, strawberry, rosemary, *Macadamia* nut oil, *Matricaria, Bifidus*, safflower oil, *Mori cortex radicis*, sage, Luffa, silk, acacia, rice, Japanese mugwort, almond, avocado, ivy, aloe, corn, olive, milk protein, *Curcuma*, soluble licorice, *ginseng, Paeonia lactiflora*, rose, *Acorus calamus, Cnidium officinale, Gardenia*, coconut, parsley, henna, horsetail, Jojoba, loess, grape seeds, pomegranate, herbs, ginger, *Kochia scoparia, Lycium chinense, Lithospermum erythrorhizon, Nelumbo nucifera* leaves, a mixture thereof, or a composite thereof, or wherein the functional chemical compound is guar gum, starch, dimethyl sulfone, locust bean gum, plant squalene, β-carotene, vitamins, a mixture thereof, or a composite thereof.

5. The method of claim 2, wherein the second solvent is methanol, ethanol, tetrahydrofuran (THF), dimethyl sulfoxide (DMSO), benzene, acetone, ethyl acetate, methylene chloride, methylethylketone, toluene, ethylene glycol diacetate, or a solvent mixture thereof.

6. The method of claim 2, wherein the concentration of polyvinyl acetate in the polymer solution is in the range of 1 wt % to 30 wt %.

7. The method of claim 2, wherein the formation of the functional extract or chemical compound-containing polyvinyl acetate film is performed by a solution casting method.

8. The method of claim 1, wherein the first solvent is an acid solution comprising a dispersant and a swelling agent, or an alkali solution comprising a dispersant and a swelling agent.

9. The method of claim 8, wherein the dispersant is sodium sulfate, sodium sulfite, calcium sulfate, magnesium sulfate, or a mixture thereof.

10. The method of claim 8, wherein the swelling agent is methanol, ethanol, propanol, ethylene glycol, propylene glycol, tetrahydrofuran (THF), dimethyl sulfoxide (DMSO), benzene, acetone, or a mixture thereof.

11. The method of claim 8, wherein the acid solution is prepared by mixing any one selected from hydrochloric acid, nitric acid, sulfuric acid, or a mixture thereof any one dispersant selected from sodium sulfate, sodium sulfite, calcium sulfate, magnesium sulfate, or a mixture thereof any one swelling agent selected from methanol, ethanol, propanol, ethylene glycol, propylene glycol, tetrahydrofuran (THF), dimethyl sulfoxide (DMSO), benzene, acetone, or a mixture thereof; and water.

12. The method of claim 8, wherein the alkali solution is prepared by mixing any one selected from sodium chloride, sodium hydroxide, potassium hydroxide, sodium bromide, sodium iodide, or a mixture thereof; any one dispersant selected from sodium sulfate, sodium sulfite, calcium sulfate, magnesium sulfate, or a mixture thereof; any one swelling agent selected from methanol, ethanol, propanol, ethylene glycol, propylene glycol, tetrahydrofuran (THF), dimethyl sulfoxide (DMSO), benzene, acetone, or a mixture thereof; and water.

13. The method of claim 8, wherein the first solvent is an alkaline solution in which sodium chloride, sodium sulfate, methanol, and water are mixed and dissolved.

14. The method of claim 1, wherein the saponification is performed at a temperature in the range of 5° C. to 80° C. for 10 hours to 300 hours.

* * * * *